United States Patent [19]
Lamberti et al.

[11] 3,988,377
[45] *Oct. 26, 1976

[54] HYDROXY SUBSTITUTED SULFOXIDES AND THIOTHERS

[75] Inventors: Vincent Lamberti, Upper Saddle River, N.J.; Henry Lemaire, Fairfield, Conn.

[73] Assignee: Lever Brothers Company, New York, N.Y.

[ * ] Notice: The portion of the term of this patent subsequent to Sept. 11, 1990, has been disclaimed.

[22] Filed: July 6, 1973

[21] Appl. No.: 376,946

Related U.S. Application Data

[60] Division of Ser. No. 113,079, Feb. 5, 1971, Pat. No. 3,758,595, which is a continuation-in-part of Ser. No. 764,362, Aug. 7, 1968, Pat. No. 3,562,337, which is a division of Ser. No. 502,299, Oct. 22, 1965, Pat. No. 3,427,248.

[52] U.S. Cl. .................. 260/609 R; 260/607 A; 252/530
[51] Int. Cl.$^2$ ....................... C07C 149/16
[58] Field of Search .................. 260/607 A, 609 R

[56] References Cited
UNITED STATES PATENTS

| | | | |
|---|---|---|---|
| 2,565,986 | 8/1951 | Olin | 260/609 R |
| 3,158,663 | 11/1964 | Brachel | 260/609 R |
| 3,522,311 | 7/1970 | Hickner | 260/607 A |
| 3,539,635 | 11/1970 | Priestley | 260/607 A |
| 3,661,851 | 5/1972 | Umbach | 260/609 R |
| 3,758,595 | 9/1973 | Lamberti et al. | 260/607 A |

FOREIGN PATENTS OR APPLICATIONS

| | | | |
|---|---|---|---|
| 1,167,202 | 10/1969 | United Kingdom | 260/609 R |

*Primary Examiner*—Lewis Gotts
*Assistant Examiner*—D. R. Phillips
*Attorney, Agent, or Firm*—Brumbaugh, Graves, Donohue & Raymond

[57] ABSTRACT

This specification relates to a detergent. More particularly, it is concerned with a detergent which is a sulfur analog of a polyolether or polyolpolyether.

13 Claims, No Drawings

HYDROXY SUBSTITUTED SULFOXIDES AND THIOTHERS

This is a division of application Ser. No. 113,079, filed Feb. 5, 1971, now issued as U.S. Pat. No. 3,758,595, which in turn is a continuation-in-part of application Ser. No. 764,362, filed Aug. 7, 1968, now issued as U.S. Pat. No. 3,562,337, which in turn is a divisional of application Ser. No. 502,299, filed Oct. 22, 1965, now issued as U.S. Pat. No. 3,427,248.

In the past a straight chain or branched chain alcohol has been reacted with ethylene oxide to form ethoxylates, such as, n-tetradecyl alcohol-7 moles ethylene oxide, dodecyl alcohol-10 moles ethylene oxide and Sterox AJ (tridecyl alcohol-about 9.5 moles ethylene oxide). These ethoxylates have detergent properties.

It has now been discovered that certain thioether analogs of polyolethers and polyolpolyethers, known also as sulfides, are surface active agents, e.g., detergent actives, dishwashing detergents, lime-soap dispersants and suds-boosters for other detergent actives. The compounds of the invention also have anti-microbial activity and are nontoxic, mild towards skin and completely biodegradable.

These new nonionic detergents have the following generic structure:

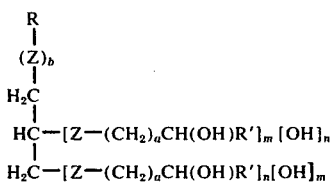

wherein R is an aliphatic hydrocarbon group having 6–14 carbon atoms; Z is oxygen, sulfur or sulfoxide but at least one Z is sulfur or sulfoxide; $a$ is 1 to 2, b is 0 or 1; $m$ is 0 or 1; $n$ is 0 or 1; $m + n$ in all occurrences is 1; and R' is H, $CH_2OH$ or $CH_3$. Subgeneric structures within the generic structure are as follows:

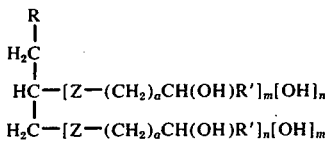

wherein R is an aliphatic saturated hydrocarbon group having 5–15 carbon atoms; Z is sulfur or sulfoxide; $a$ is 1 or 2; $m$ is 0 or 1; $n$ is 0 or 1; $m+n$ in all occurrences is 1; and R' is H, $CH_2OH$ or $CH_3$.

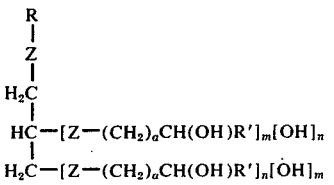

wherein R is an aliphatic saturated hydrocarbon group having 6–14 carbon atoms; Z is oxygen, sulfur or sulfoxide but at least one Z is sulfur or sulfoxide; $a$ is 1 or 2; $m$ is 0 or 1; $n$ is 0 or 1; $m + n$ in all occurrences is 1; and R' is H, $CH_2OH$ or $CH_3$. As used herein, these structures are intended to include isomeric compounds.

Any known method may be employed to prepare the aforementioned sulfur analogs of polyolethers and polyolpolyethers. One method is to react a long chain epoxide or long chain glycidyl ether with hydroxy alkyl mercaptans, such as, 2-mercapto-ethanol, 3-mercapto-1,2-propanediol, 1-mercapto-2-propanol, 3-mercapto-1-propanol, 4-mercapto-1,2,butanediol and 4-mercapto-2-butanol, in the presence of a basic catalyst, e.g., $NaOCH_3$. The reaction can also be carried out without a catalyst, but in such cases, longer reaction times are required. In accordance with this method, the compounds of the invention are the reaction products of:

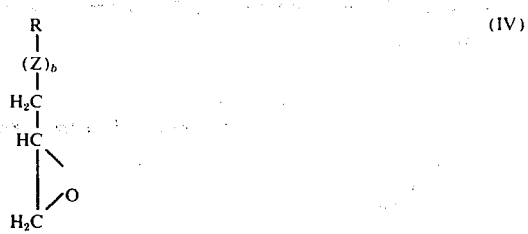

with:

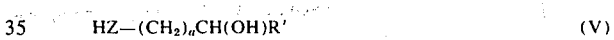

wherein R, $a$, b and R' are as defined heretofore and Z is oxygen or sulfur but at least one Z is sulfur. The thioether reaction product can be oxidized, for example with t-butyl hydroperoxide in methanol, to form the corresponding sulfoxide. It is also possible to react either a long-chain diol containing sulfur or a monoalkyl thioether of glycerol with one molar proportion of ethylene oxide. By this process, however, a mixture of products is obtained containing large proportions of unreacted starting diol or thioether, with some monoethoxylated compound with which this invention is concerned, and with some poly-ethoxylated compounds such as those represented by the formula

wherein $x$ is greater than 1.

If a long-chain sulfur-containing epoxyalkane is a reactant, it may be obtained by any suitable method. For example, long chain mercaptans can be reacted with epichlorohydrin to form 3-alkylthio-2-hydroxy-1-chloropropanes which, in turn, are reacted with strong aqueous sodium hydroxide to produce alkyl glycidyl thioethers. Similarly, if a long-chain sulfur-containing diol is a reactant, it may be obtained by any suitable method such as the reaction of hydrogen sulfide with long chain epoxides.

The following short-chain polyhydroxy reactants among others are within the scope of the above structure I:

| Short-chain polyhydroxy reactant (Structure V) | | | | |
|---|---|---|---|---|
| a | R' | Z | Name | Structure |
| 1 | H | O | ethylene glycol | HOCH₂CH₂OH |
| 1 | CH₂OH | O | glycerol | HOCH₂CH(OH)CH₂OH |
| 1 | CH₃ | O | 1,2-propanediol | HOCH₂CHOHCH₃ |
| 1 | H | S | 2-mercapto ethanol | HSCH₂CH₂OH |
| 1 | CH₂OH | S | 3-mercapto-1,2-propanediol | HSCH₂CH(OH)CH₂OH |
| 1 | CH₃ | S | 1-mercapto-2-propanol | HSCH₂CHOHCH₃ |
| 2 | H | O | 1,3-propanediol | HO-CH₂-CH₂-CH₂OH |
| 2 | CH₂OH | O | 1,2,4-butanetriol | HOCH₂CH₂OH(OH)CH₂OH |
| 2 | CH₃ | O | 1,3-butylene glycol | HOCH₂CH₂CH(OH)CH₃ |
| 2 | H | S | 3-mercapto-1-propanol | HSCH₂CH₂CH₂OH |
| 2 | CH₂OH | S | 4-mercapto-1,2-butanediol | HSCH₂CH₂CH(OH)CH₂OH |
| 2 | CH₃ | S | 4-mercapto-2-butanol | HSCH₂CH₂CH(OH)CH₃ |

Preferred types of compounds in this invention, among others, include sulfides having the following structures:

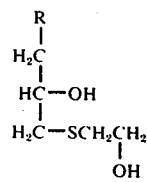

2-hydroxyalkyl 2'-hydroxyethyl sulfide (VI)

(b = O; R' = H)

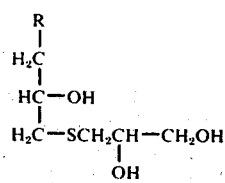

2-hydroxyalkyl 2',3'-dihydroxypropyl sulfide (VII)

(b = O; R' = CH₂OH)

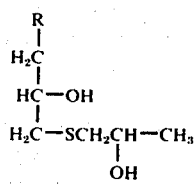

2-hydroxyalkyl 2'-hydroxypropyl sulfide (VIII)

(b = O; R' = CH₃)

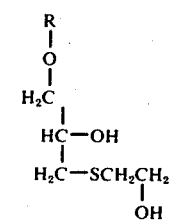

(2-hydroxy-3-alkoxy)propyl 2'-hydroxyethyl sulfide (IX)

(b = 1; Z = O; R' = H)

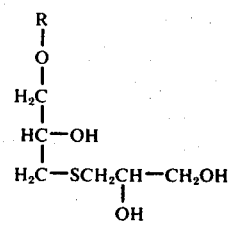

(2-hydroxy-3-alkoxy)propyl 2',3'- dihydroxypropyl sulfide (b = 1; Z = O; R' = CH₂OH)  (X)

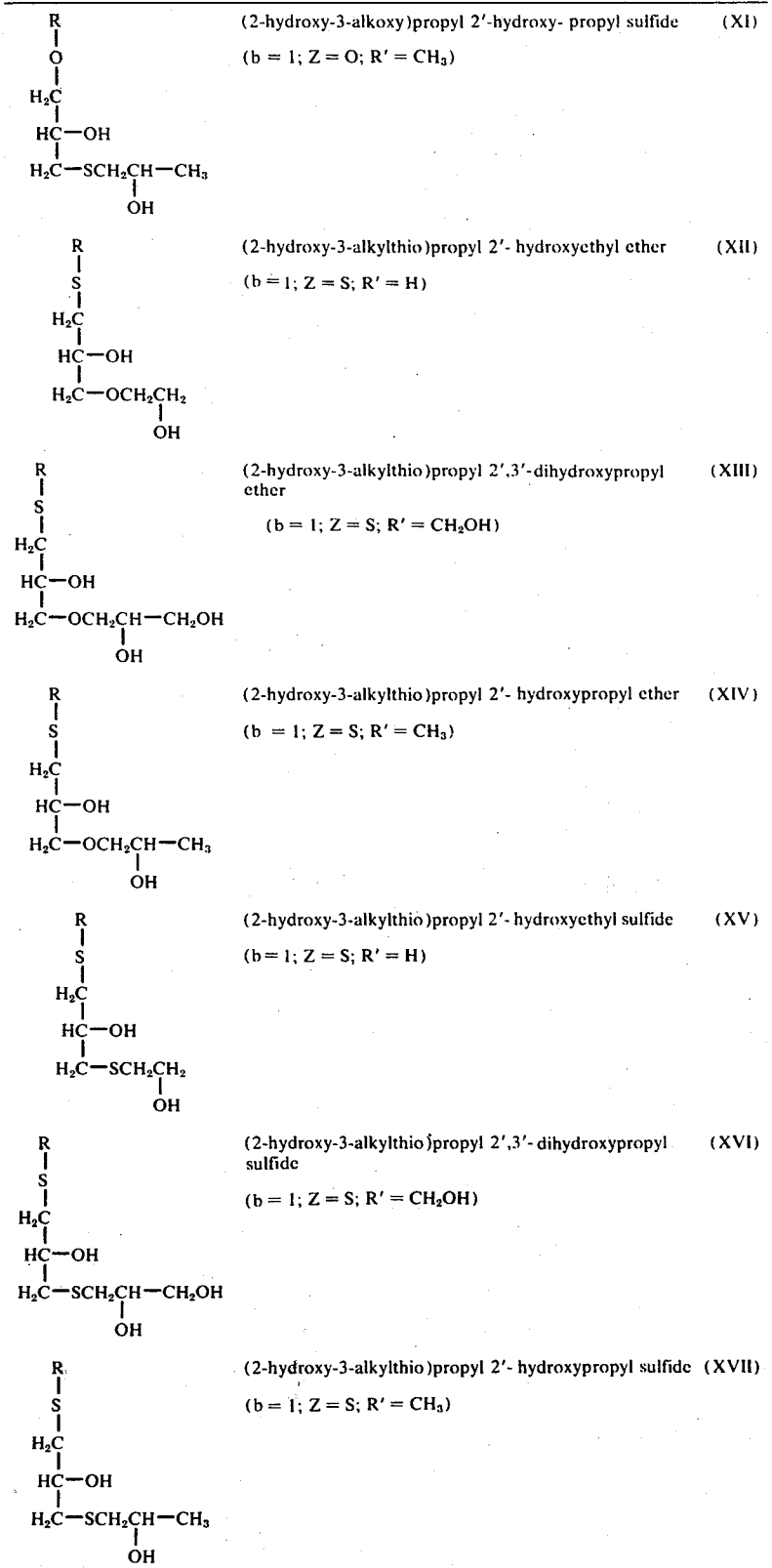

wherein R in structures VI to XVII is an aliphatic saturated hydrocarbon group having 5–15 carbon atoms. The corresponding sulfoxides for structures VI to XVII are also suitable for the present invention.

Suitable specific compounds of this invention, among others, include sulfides such as 2-hydroxyundecyl 2′-hydroxyethyl sulfide; 2-hydroxydodecyl 2′-hydroxyethyl sulfide; 2-hydroxy-$C_{11}$-$C_{14}$ alkyl 2′-hydroxyethyl sulfide; 2-hydroxydodecyl 2′,3′-dihydroxypropyl sulfide; 2-hydroxydodecyl 2′-hydroxypropyl sulfide; (2-hydroxy-3-decyloxy) 2′-hydroxyethyl sulfide; (2-hydroxy-3-dodecyloxy)propyl 2′,3′-dihydroxypropyl sulfide; (2-hydroxy-3-decyloxy)propyl 2′-hydroxypropyl sulfide; (2-hydroxy-3-dodecylthio)propyl 2′-hydroxyethyl ether; (2-hydroxy-3-tetradecylthio)propyl 2′,3′-dihydroxypropyl ether; (2-hydroxy-3-dodecylthio)propyl 2′-hydroxypropyl ether; (2-hydroxy-3-dodecylthio)propyl 2′-hydroxyethyl sulfide; (2-hydroxy-3-tetradecylthio)propyl 2′,3′-dihydroxypropyl sulfide; (2-hydroxy-3-dodecylthio)propyl 2′-hydroxypropyl sulfide; and corresponding sulfoxides thereof.

The compounds of the present invention may be used alone as detergents. However, the compounds of the invention may also be used in combination with other detergents. Examples of the detergent compounds with which the compounds of the invention may be admixed to form superior combinations are the well-known anionic types represented by the water-soluble and water-dispersible organic surface-active agents having in the molecule a hydrophobic group of about 8 to about 22 carbon atoms and a hydrophilic sulfate, sulfonate or carboxylic group having a cation which does not insolubilize the compound. The following anionic detergents, among others, are suitable for use with the compounds of the present invention:

1. Alkylbenzenesulfonates, such as sodium and potassium salts having a branched or straight chain alkyl portion of about 9 to about 15 carbon atoms.
2. Alkyl sulfates, such as the sodium and triethanol-ammonium salts of $C_{10}$–$C_{20}$ alkyl sulfuric acid, prepared by sulfating the alcohols derived from coconut oil or tallow, or prepared synthetically.
3. The alkali metal and ammonium salts of the sulfated ethoxylates of a long-chain alcohol and 3 to 5 molar proportions of ethylene oxide, for example, the ammonium salt of an ethoxylate containing an average of 3.1 molar proportions of ethylene oxide and 1 mole of an alcohol mixture known commercially as Alfol 1412, composed of about ⅔ n-tetradecanol and about ⅓ n-dodecanol.
4. The compounds known as "Medialans", which are amido carboxylic acids formed by condensing fatty acids of $C_8$–$C_{22}$ chain length with sarcosine, $CH_3NHCH_2COOH$. Generally the alkali metal and basic nitrogen-radical salts are employed.
5. Alkanesulfonates, such as ammonium dodecane-sulfonate.
6. Alkoxyhydroxypropanesulfonates, such as the water-soluble salts of 3-dodecyloxy-2-hydroxy-1-propane-sulfonate.
7. Soaps, the surface-active substances formed usually by the reaction of caustic alkalies with natural glyceridic fats and oils, generally prepared in high purity, and having the generic molecular formula RCOONa, wherein R is a straight-chain hydrocarbon group having from about 7 to about 21 atoms.
8. Olefine sulfonates, such as dodecene sulfonate, and the compounds described in U.S. Pat. No. 3,332,880.

The compounds of the invention are also suds-boosters for nonionic detergents. The following nonionic detergents, among others, are suitable for use with the compounds of the present invention:

1. The Pluronics, formed by condensing propylene oxide with propylene glycol to a molecular weight of about 600–2500 to form a base followed by condensing ethylene oxide to this base to the extent of about 10% to about 90%, total molecule basis. U.S. Pat. Nos. 2,674,619 and 2,677,700 describe operable nonionic compounds.
2. Compounds formed by the simultaneous polymerization of propylene oxide and ethylene oxide, and containing randomly positioned oxypropylene and oxyethylene groups. These and related compounds are described in U.S. Pat. Nos. 2,979,528, 3,036,118, 3,022,335, 3,036,130 and 3,048,548.
3. Alkyl phenols having 9–12 carbon atoms in the alkyl portion, (straight or branched) ethoxylated with 4–10 molar proportions of ethylene oxide.
4. Ethoxylates of fatty alcohols having 8–18 carbon atoms per molecule and 5–30 molar proportions of oxyethylene groups.

In addition to being suds-boosters for the above detergents, the compounds of this invention act as suds-boosters for ampholytic compounds such as hydroxyalkyl methyl taurates and zwitterionic surface-active substances, such as coco dimethyl sulfopropyl betaine.

The compounds of this invention may interact synergistically with all suds-producing surfaceactive substances to provide mixtures having improved properties beyond those expected on the basis of the properties of the individual components of the mixture. With non-soaps, the synergism may be evident in suds production or stability. With soaps, the synergism may be evident in the form of reduced lime-soap scum formation.

Thus, in accordance with this invention, new compounds have been formed. The compounds of the present invention have certain noteworthy features. For example, the synergistic suds-producing properties of the compounds with other detergents and sudsing agents are surprising. The antimicrobial properties of the compounds are also surprising. Furthermore, the compounds of the invention are nonionic surfactants with foaming characteristics superior to both well-known anionic and nonionic detergents. The ability to formulate a detergent based on the nonionic materials of the invention having high foaming or dishwashing characteristics with built-in germicidal properties and which at the same time is biodegradable by sewage or natural water bacteria is certainly surprising and unexpected.

The following examples are submitted to illustrate but not to limit this invention. Unless otherwise indicated, all parts and percentages in the specification and claims and based upon weight.

EXAMPLE I

Compound A, 2-hydroxydodecyl 2′-hydroxyethyl sulfide, was prepared by stirring a mixture of 25.3 g. (0.325 moles) of 2-mercaptoethanol and 5.4 g. (0.1 mole) of sodium methoxide under nitrogen while adding dropwise 55.1 g. (0.324 moles) of 1,2-epoxydodecane over a period of 25 minutes. After continued stirring on a steam bath for 85 minutes, the crude material was cooled and dissolved in hexane. A portion therefrom was washed with water in the presence of methanol to remove the catalyst and another portion was merely filtered. Evaporation of the hexane in each case afforded the desired product, 2-hydroxydodecyl 2′-hydroxyethyl sulfide.

Compound B, 2-hydroxy-$C_{11}$-$C_{14}$ alkyl 2'-hydroxyethyl sulfide, was prepared in the same manner except that 1,2 epoxy $C_{11}$-$C_{14}$ alkane was used as one of the reactants.

Compound C, a sulfoxide compound, 2-hydroxydodecyl 2'-hydroxyethyl sulfoxide, was formed by oxidizing Compound A, 2-hydroxydodecyl 2'-hydroxyethyl sulfide, with t-butyl hydroperoxide in methanol. More specifically, a solution of 8 g. of 2-hydroxydodecyl 2'-hydroxyethyl sulfide in 38 ml. of methanol was treated with 3 g. of t-butyl hydrogen peroxide and heated at 50° C. for 2 days. The solvent was evaporated and the crystals washed with hexane.

The dishwashing properties of the compounds prepared according to Examples A, B and C were determined by ascertaining the number of plates washed in duplicate tests with 1.8 g. of each of the above compounds in 6 quarts of 120 ppm water at 116° F., both with or without 0.54 g. of coconut fatty acid monoethanolamide (CMEA). The results are shown in Table 1.

Table 1

| Compound | Boosted with CMEA | No. of Dishes Washed |
|---|---|---|
| A | No | 20–24 |
| B | No | 20 |
| A | Yes | 38–42 |
| B | Yes | 42 |
| C | Yes | 42 |

This example shows that the sulfides and a corresponding sulfoxide within the purview of the present invention have excellent dishwashing properties.

EXAMPLE II

The compounds listed in Table 2 are other compounds that are considered to be suitable detergents. They may be prepared by the same procedure described in Example I by varying the reactants to provide the required end product.

Table 2

2-hydroxyundecyl 2'-hydroxyethyl sulfide;
2-hydroxydodecyl 2',3'-dihydroxypropyl sulfide;
2-hydroxydodecyl 2'-hydroxypropyl sulfide;
(2-hydroxy-3-decyloxy)propyl 2'-hydroxyethyl sulfide;
(2-hydroxy-3-dodecyloxy)propyl 2',3'-dihydroxypropyl sulfide;
(2-hydroxy-3-decyloxy)propyl 2'-hydroxypropyl sulfide;
(2-hydroxy-3-dodecylthio)propyl 2'-hydroxyethyl ether;
(2-hydroxy-3-tetradecylthio)propyl 2',3'-dihydroxypropyl ether;
(2-hydroxy-3-dodecylthio)propyl 2'-hydroxypropyl ether; (2-hydroxy-3-dodecylthio)propyl 2'-hydroxyethyl sulfide;
(2-hydroxy-3-tetradecylthio)propyl 2',3'-dihydroxypropyl sulfide;
(2-hydroxy-3-dodecylthio)propyl 2'-hydroxypropyl sulfide;
and corresponding sulfoxides thereof.

EXAMPLE III

The germicidal activity of several compounds described in this invention was determined by the Streak Gradient Plate Method.

The Streak Gradient Plate Method is a modification of the gradient plate method of Szybalski, Science 116: 46–48 (1952), for the determination of germicide MEC (Minimum Effective Concentration) values. This method employs streaks of several organisms per plate.

As shown in Table 3, certain compounds of the invention have surprisingly high antimicrobial activity and they are superior to well-known germicides and soaps against a number of micro-organisms.

TABLE 3

| | Germicidal Activity by the Gradient Streak Plate Method | | | | |
|---|---|---|---|---|---|
| | Minimum Effective Concentration (MEC) in ppm | | | | |
| Compound | Sa | Mc | Sf | Ca | An |
| 2-hydroxydodecyl hydroxyethyl sulfide | 36 | 51 | 25 | 34 | 18 |
| 2-hydroxy $C_{11}$–$C_{14}$ alkyl 2'-hydroxyethyl sulfide | 50 | 111 | 28 | 100 | 27 |
| Controls: | | | | | |
| Alfonic 1418-6 (Alfol 1418-62.5% EO) | >10,000 | — | — | — | — |
| Sterox DJ (Dodecylphenol-10EO) | >10,000 | — | — | — | — |
| Igepon A (coconut) | 1780 | 3550 | 5000 | 3900 | 1660 |
| Soap (LTS) | 1550 | 1880 | 2200 | 1610 | 455 |

Culture Codes:
Sa - S.aureus
Mc - M.candidus
SF - Strep.faecalis
Ca - C.albicans
An - A.niger Having set forth the general nature and specific embodiments of the present invention, the true scope is now particularly pointed out in the appended claims.

What is claimed is:

1. A detergent having the structure:

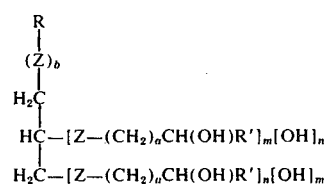

wherein R is an aliphatic hydrocarbon group having 5–15 carbon atoms; Z is oxygen, sulfur or sulfoxide but at least one Z is sulfur or sulfoxide; $a$ is 1 or 2; $b$ is 0 or 1; $m$ is 0 or 1; $n$ is 0 or 1; $m+n$ in all occurrences is 1; and R' is H, $CH_2OH$ or $CH_3$.

2. The detergent according to claim 1 having the structure:

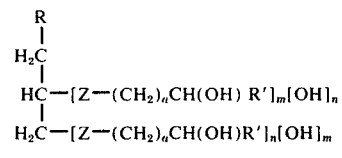

wherein R is an aliphatic saturated hydrocarbon group having 5–15 carbon atoms; Z is sulfur or sulfoxide; $a$ is 1 or 2; $m$ is 0 or 1; $n$ is 0 or 1; $m+n$ in all occurrences is 1; and R' is H, $CH_2OH$ or $CH_3$.

3. The detergent according to claim 1 having the structure:

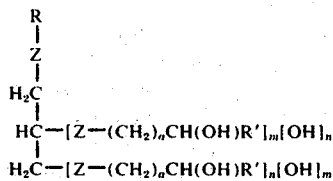

wherein R is an aliphatic saturated hydrocarbon group having 6–14 carbon atoms; Z is oxygen, sulfur or sulfoxide; $a$ is 1 or 2; $m$ is 0 or 1; $n$ is 0 or 1; $m+n$ in all occurrences is 1; and R' is H, $CH_2OH$ or $CH_3$.

4. The detergent according to claim 1 which is 2-hydroxyundecyl 2'-hydroxyethyl sulfide.

5. The detergent according to claim 1 which is 2-hydroxydodecyl 2',3'-dihydroxypropyl sulfide.

6. The detergent according to claim 1 which is 2-hydroxydodecyl 2'-hydroxypropyl sulfide.

7. The detergent according to claim 1 which is (2-hydroxy-3-decyloxy)propyl 2'-hydroxyethyl sulfide.

8. The detergent according to claim 1 which is (2-hydroxy-3-dodecyloxy)propyl 2',3'-dihydroxypropyl sulfide.

9. The detergent according to claim 1 which is (2-hydroxy-3-decyloxy)propyl 2'-hydroxypropyl sulfide.

10. The detergent according to claim 1 which is (2-hydroxy-3-dodecylthio)propyl 2'-hydroxyethyl ether.

11. The detergent according to claim 1 which is (2-hydroxy-3-dodecylthio)propyl 2'-hydroxypropyl ether.

12. The detergent according to claim 1 which is (2-hydroxy-3-dodecylthio)propyl 2'-hydroxyethyl sulfide.

13. The detergent according to claim 1 which is (2-hydroxy-3-dodecylthio)propyl 2'-hydroxypropyl sulfide.

* * * * *